(12) United States Patent
Chown

(10) Patent No.: US 6,419,122 B1
(45) Date of Patent: Jul. 16, 2002

(54) MAGNETICALLY OPERATED APPARATUS FOR DISPENSING A CHEMICAL

(76) Inventor: Peter Arthur Charles Chown, Strawberry House, Foldgate Lane, Magdalen, King's Lynn, Norfolk, PE34 3DA (GB)

( * ) Notice: Subject to any disclaimer, the term of this patent is extended or adjusted under 35 U.S.C. 154(b) by 0 days.

(21) Appl. No.: 09/674,244
(22) PCT Filed: Apr. 12, 1999
(86) PCT No.: PCT/GB99/01115
§ 371 (c)(1),
(2), (4) Date: Oct. 27, 2000
(87) PCT Pub. No.: WO99/55392
PCT Pub. Date: Nov. 4, 1999

(30) Foreign Application Priority Data

Apr. 29, 1998 (GB) .............................................. 9809215
Jul. 13, 1998 (GB) .............................................. 9815160

(51) Int. Cl.[7] .................................................. A61L 9/12
(52) U.S. Cl. ......................... 222/162; 222/336; 222/645
(58) Field of Search ........................... 222/153.04, 162, 222/336, 504, 645, 649

(56) References Cited

U.S. PATENT DOCUMENTS

| | | | |
|---|---|---|---|
| 3,187,949 A | 6/1965 | Mangel | 222/649 |
| 3,666,144 A | 5/1972 | Winder | 222/646 |
| 3,972,447 A | 8/1976 | Fegley | 222/5 |
| 4,079,862 A * | 3/1978 | Fegley | 222/162 |
| 4,415,797 A | 11/1983 | Choustoulakis | 219/273 |
| 4,483,466 A * | 11/1984 | Gutierrez | 222/647 |
| 5,791,520 A | 8/1998 | Tichenor | 222/82 |
| 5,938,076 A * | 8/1999 | Ganzeboom | 222/23 |

FOREIGN PATENT DOCUMENTS

| | | | |
|---|---|---|---|
| EP | 0 567 678 A1 | 4/1992 | ........... A61B/19/00 |
| GB | 1021586 | 11/1963 | |

* cited by examiner

Primary Examiner—John Kwon
Assistant Examiner—Patrick Buechner
(74) Attorney, Agent, or Firm—Iandiorio & Teska

(57) ABSTRACT

Apparatus (2), for dispensing a chemical, including an aerosol container (10), which contains the chemical, the aerosol container provided with magnetic material, a solenoid (12) which extends around the aerosol container (10), and a control switch (16) and timer (18) to control actuation of the solenoid (12). The actuation of the solenoid (12) causes the aerosol container (10) to behave as the solenoid core and the aerosol container (10) moves from a non-dispensing position to a dispensing position.

10 Claims, 3 Drawing Sheets

MAGNETICALLY OPERATED APPARATUS FOR DISPENSING A CHEMICAL

FIELD OF THE INVENTION

This invention relates to apparatus for dispensing a chemical.

PRIOR ART

Chemicals in the form of air fresheners are traditionally used in the form of blocks or gels which vaporise, or in the form of aerosols. The blocks or gels are usually contained in a container which, when opened, constantly releases the air freshening chemical over a period. This type of air freshener is only effective for a few days because the air freshener is constantly being dispensed and the human brain tends to get used to the smell after a few days and then the air freshening smell is no longer noticed and is thus no longer effective. A further problem with the blocks or gels is that air movement is required to spread the air freshener and therefore its aroma effectively around a room. The aerosol sprays do not suffer from the problem of being constantly released because they have to be manually operated. However, it is not always convenient to have to manually operate an aerosol spray. Still further, the spray is effective for a very short period only as the sprayed chemical does not stay airborne for very long.

BRIEF DESCRIPTION OF THE INVENTION

It is an aim of the present invention to obviate or reduce the above mentioned problems.

Accordingly, the present invention provides apparatus for dispensing a chemical, which apparatus comprises an aerosol container which contains the chemical, electromagnetic means, and control means, the electromagnetic means being operable between a first state in which the chemical is not dispensed from the aerosol container and a second state in which the chemical is dispensed from the aerosol container, and the control means being such as to control the operation of the electromagnetic means such that the electromagnetic means is in the second state for predeterminable periods, and the apparatus being characterised in that the electromagnetic means extends around the aerosol container, and magnetically attractable material is provided for the aerosol container such that the aerosol container is able to be moved by the electromagnetic means for the purpose of dispensing the chemical from the aerosol container.

The apparatus may be one in which the electromagnetic means causes the aerosol container to move such that when the electromagnetic means goes from the first state to the second state then the aerosol container is caused to move to a position in which it releases the chemical, and when the electromagnetic means goes from the second state to the first state then the aerosol container is caused to move to a position in which it does not release the chemical. Other arrangements may be employed if desired.

Preferably, the aerosol container has an outlet valve which is depressed when the aerosol container is caused to move to the position in which it releases the chemical.

The aerosol container may be mounted on spring means which biases the aerosol container towards the position in which it releases the chemical. The spring means is preferably a coil spring but other types of spring means may be employed.

The aerosol container may be made of the magnetically attractable material. In this case, the electromagnetic means is able to attract the aerosol container when the aerosol container has to be moved. The aerosol container may be made of a magnetically attractable material such for example as a ferrous material.

Many aerosol containers currently manufactured are made of aluminium or a plastics material. The aluminium or the plastics material is a non-magnetically attractable material which means that the electromagnetic means would not normally be able to attract by magnetism the aerosol container. This problem may be overcome in two ways. Firstly, the aerosol container may be made of a non-magnetically attractable material which is then provided with the magnetically attractable material, for example in the form of a plate or a ring secured to the outer wall of the aerosol container. Secondly, the problem may be overcome by having the aerosol container made of the non-magnetically attractable material and then having the aerosol container being held in a holder made of the magnetically attractable material. The holder can then be magnetically attracted by the electromagnetic means, in which case the aerosol container will move with the holder. The aerosol container can be arranged to be a removable fit in the holder so that the aerosol container can easily be replaced when it is empty.

The electromagnetic means and the control means may be battery powered and/or mains powered and/or solar powered. When the electromagnetic means and the control means are battery powered, then the apparatus may include a battery compartment for one or more batteries.

The electromagnetic means may be a solenoid. Other types of electromagnetic means may however be employed.

The control means may be a switch. The switch may be a manually operated switch. The manually operated switch may be a push button switch or a lever switch.

The apparatus of the invention may include a housing. The precise shape and size of the housing will normally depend upon the intended use of the apparatus of the invention. Thus, for example, if the apparatus is to be used in a room to dispense a chemical into the air, then the housing will usually be small and it may be of a circular, square or rectangular shape. If the apparatus is to be used in a vacuum cleaner, then the housing may be a housing of the vacuum cleaner.

The apparatus of the invention may be such as to spray direct where the chemical is required, for example into the air or direct on to furnishings such for example as a carpet or curtains. In this case, the aerosol container will normally be positioned substantially adjacent an outlet where the direct spraying is required.

Alternatively, if desired, the apparatus may include conduit means for extending from the aerosol container to a position in which the chemical is required to be released. In this case, the aerosol container and its associated electromagnetic means may be positioned relatively remote from the area where the chemical is required to be released.

The chemical in the aerosol container may be any of the known chemicals currently dispensed from aerosol containers, including liquids and powders. If the chemical is for use on a carpet, then the chemical may be to make the carpet smell fresh and/or to control pests such for example as carpet mites. The chemical may consist of or contain a fragrance for giving fragrant air and removing the smell which is very commonly associated with vacuum cleaners as dust bags or dust compartments fill up with dirt. Dry powder chemicals may be dispensed with electrical safety from the vacuum cleaner. Where the chemical is a liquid, then appropriate safety features should be employed to ensure that the liquid spray does not contact current-carrying parts of the vacuum cleaner.

BRIEF DESCRIPTION OF THE DRAWINGS

Embodiments of the invention will now be described solely by way of example and with reference to the accompanying drawings in which.

DETAILED DESCRIPTION OF THE DRAWINGS

Figure 1:
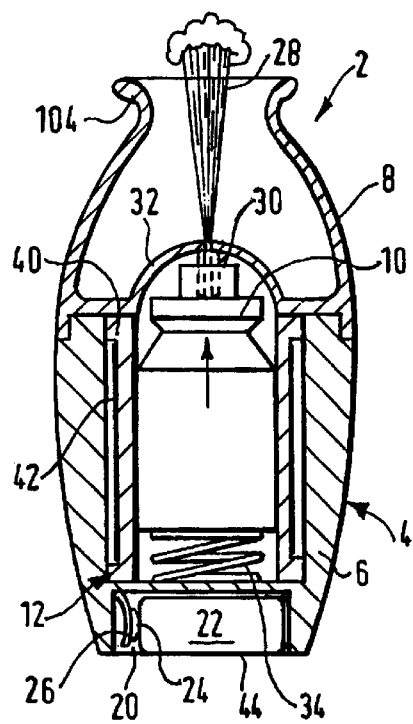
FIG. 1 is a section through first apparatus for dispensing a chemical, the apparatus being shown in an active state in which the chemical is dispensed.

Referring to FIGS. 1–4, there is shown apparatus 2 for dispensing a chemical. The apparatus 2 comprises a housing 4, the housing 4 comprises a lower part 6 and an upper part 8 which screws to the lower part 6.

The apparatus 2 comprises an aerosol container 10 which is located as shown in the lower part 6 of the housing 4. The upper part 8 of the housing 4 is removable from the lower part 6 in order to enable the aerosol container 10 to be inserted in position, and to be replaced when empty with a full aerosol container 10.

Figure 4:
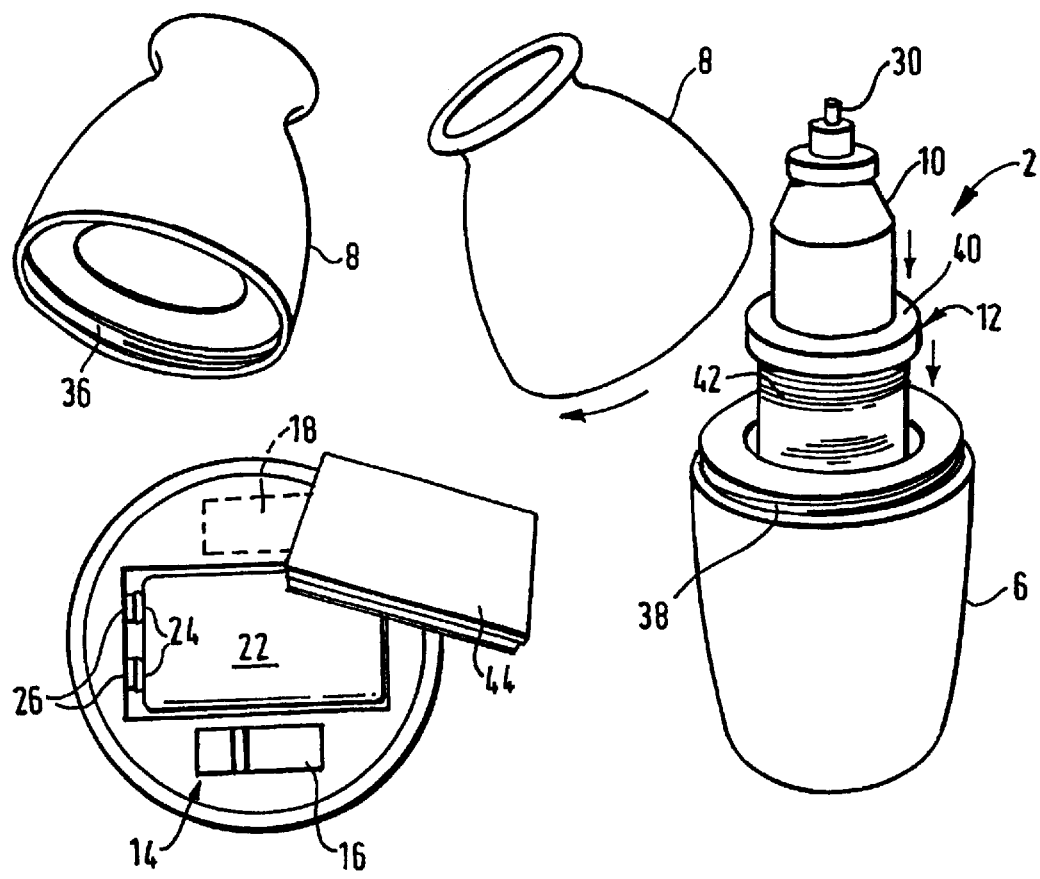
FIG. 4 is an exploded perspective view of various parts of the apparatus shown in FIG. 1.

The apparatus 2 has electromagnetic means in the form of a battery-operated solenoid 12. The solenoid 12 is controlled by battery-operated control means 14. As shown in FIG. 4, the control means 14 includes an on/off switch 16 and a timer circuit 18.

The housing 4 includes a battery compartment 20 for a battery 22. The battery 22 has a terminal 24 which presses on a sprung terminal 26 which forms part of the control means 14. The battery 22 is for providing the electrical power for the solenoid 12 and the control means 14.

Figure 2:
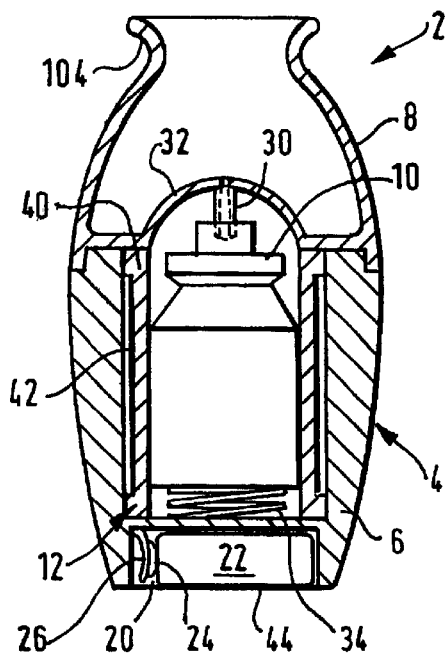
FIG. 2 is a section like FIG. 1 except that the apparatus is in a condition in which the chemical is not being dispensed.
Figure 3:
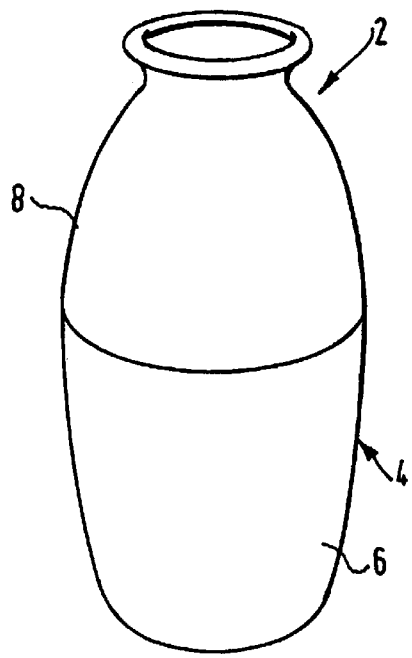
FIG. 3 is a perspective view of the apparatus shown in FIG. 1.

The solenoid 12 is operable between a first state as shown in FIG. 2 in which the chemical is not dispensed from the aerosol container 10, and a second state as shown in FIG. 1 in which the chemical is dispensed from the aerosol container 10. The control means 14 is such as to control the operation of the solenoid 12 such that the solenoid 12 is in the second state for predeterminable periods of time. Thus the control means 14 is able to ensure that the apparatus 2 dispenses chemical in the form of a spray 28 for predeterminable periods of time and/or at predeterminable intervals.

As can be seen from a comparison of FIGS. 1 and 2, the solenoid 12 causes the aerosol container 10 to move such that when the solenoid 12 goes from the first state to the second state, then the aerosol container 10 is caused to move to a position as shown in FIG. 1 in which it releases the chemical. When the solenoid 12 goes from the second state to the first state, then the aerosol container 10 is caused to move to the position shown in FIG. 2 in which it does not release the chemical.

As can be seen from FIGS. 1, 2 and 4, the solenoid 12 is positioned in the lower part 6 of the housing 4. Also, the solenoid 12 extends around the outside of the aerosol container 10. The movement of the aerosol container 10 takes place due to the fact that the aerosol container 10 is made of a ferrous material which is a magnetically attractable material. When the solenoid 12 is activated, a magnetic field is generated, allowing the aerosol container 10 to be attracted to the appropriate pole of this magnetic field, giving rise to a movement of the aerosol container 10. When the solenoid 12 is de-activated, the aerosol container 10 is no longer attracted to the appropriate pole of the magnetic field and the aerosol container 10 can then move back to its stand-by position.

The aerosol container 10 has an outlet valve 30 which is depressed when the aerosol container 10 is caused to move to the position shown in FIG. 1 in which the aerosol container 10 releases the chemical. The upper part 8 has a bridge portion 32 which presses against the outlet valve 30 in the non-operative condition of the apparatus 2 as shown in FIG. 2. When the aerosol container 10 moves from the position shown in FIG. 2 to the position shown in FIG. 1, then the outlet valve 30 become depressed and the aerosol container 10 is able to dispense the spray 28. The aerosol container 10 is mounted on spring means in the form of a coil spring 34. The coil spring 34 biases the aerosol container 10 towards the position shown in FIG. 1 in which the aerosol container 10 releases the spray 28. As is well known, the aerosol container 10 is such that the outlet valve 30 is spring biased to its closed position. The biasing force of the coil spring 34 is less than the biasing force in the aerosol container 10 keeping the outlet valve 30 closed. Thus the biasing force of the coil spring 34 is to help the solenoid 12 when it is activated. The help afforded by the coil spring 34 enables a saving in battery power and/or the use of a smaller solenoid.

As can be seen from FIG. 4, the upper part 8 of the housing 4 is shown in two positions. The left hand position shown in FIG. 4 illustrates how the upper part 8 is provided with an internal screw thread 36 for screwing over an external screw thread 38 on the lower part 6 of the housing 4. As can best be seen in FIG. 4, the solenoid 12 has a body 40 and windings 42. As also seen in FIG. 4, the battery compartment 20 is closed by a lid 44 which clips into position.

Figure 5:
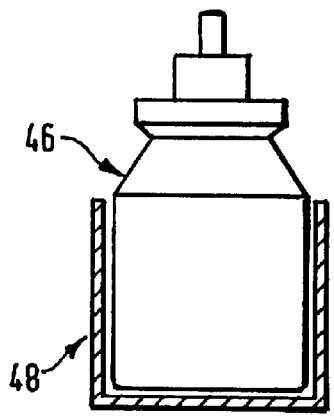
FIG. 5 illustrates a modification to the apparatus shown in FIGS. 1–4.

Referring to FIG. 5, there is shown an aerosol container 46 which is made of aluminium. The aluminium is a non-magnetically attractable material. In order to enable the aerosol container 46 to move when the solenoid 12 is activated, the aerosol container 46 is held in a holder 48. The holder 48 is made of a magnetically attractable material.

Figure 6:
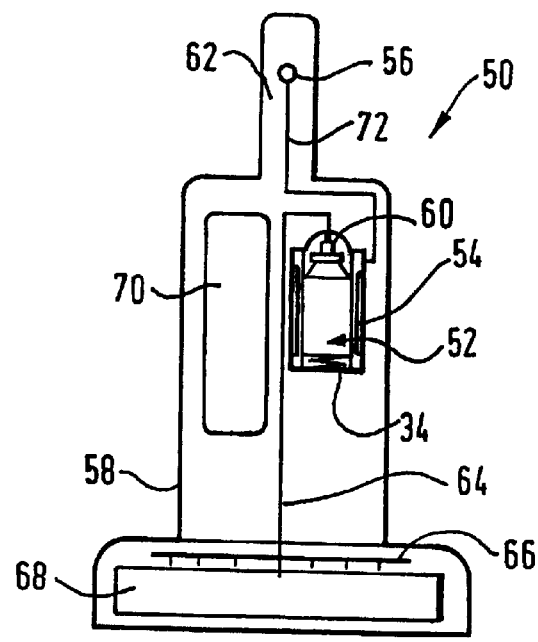
FIG. 6 shows second apparatus for dispensing a chemical.
Figure 7:
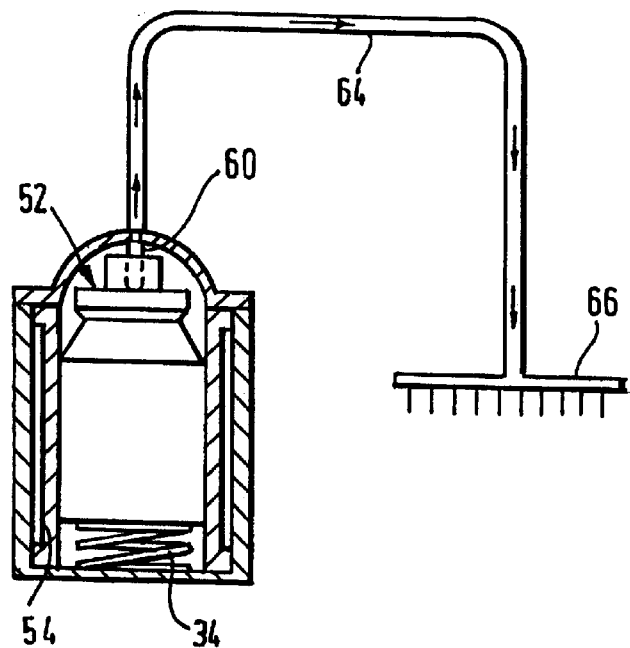
FIG. 7 shows in more detail parts of the apparatus shown in FIG. 6.

Referring to FIGS. 6 and 7, there is shown apparatus 50 which is in the form of an upright vacuum cleaner and which is for dispensing a chemical. The vacuum cleaner may be regarded as a standard vacuum cleaner additionally provided with an aerosol container 52, electromagnetic means in the form of a solenoid 54, and control means 56. The apparatus 50 has a housing 58 which is the normal housing of a vacuum cleaner.

The aerosol container 52 is so located in the housing 58 that its valve 60 is ready for being depressed when the aerosol container 52 is moved to a dispensing condition. This movement of the aerosol container 52 is effected by activation of the solenoid 54.

The control means 56 is in the form of a push button switch mounted on a handle 62 of the apparatus 50. Depression of the control means 56 causes the solenoid 54 to operate from a first state in which the chemical is not dispensed from the aerosol container 52, to a second state in which the chemical is dispensed from the aerosol container 52. As chemical from the aerosol container 52 is dispensed, it passes along conduit means 64 to a dispensing head 66. At the dispensing head 66, the chemical is dispensed on to a rotary brush 68 of the apparatus 50. The chemical is thus able to be dispensed directly on to a carpet, for the purpose of making the carpet smell fresh and/or killing pests such for example as carpet mites. A fragrant smell may be dispensed from the aerosol container 52 in order to give fragrant air and remove the smell which is very common with vacuum cleaners when dust bags or dust compartments begin to fill up.

The solenoid 54 is mains operated so that it will only be able to be operated when the main vacuum motor (not shown) of the apparatus 50 is operating. This provides a safety feature for avoiding unwanted dispensation of the chemical from the aerosol container 52.

It is to be appreciated that the embodiments of the invention described above with reference to the accompanying drawings have been given by way of example only and that modifications may be effected. Thus, for example, the apparatus 2 may be of a shape other than that shown. The apparatus 2 may be used to dispense any suitable and appropriate chemical or combinations of chemicals. Thus, for example, the chemical may be at least one of an air freshener, a medicament, a fly killer, an insecticide and a pesticide. The air freshener may be used for freshening rooms. The medicament may be used in a room such as a bedroom where a person is sleeping at night in order, for example, to assist a person in breathing if the medicament is for being inhaled in order to assist persons breathing. The fly killer may be for killing flies. The insecticide and the pesticide may be for killing insects and pests. If desired, the apparatus 2 may be used for dispensing a chemical directly into a person's mouth, in which case the apparatus 2 forms inhaler apparatus. A person's mouth may be positioned around the lip 104 of the apparatus 2. Where the chemical being dispensed is a medicament, then the medicament may be used to help persons suffering from asthma to breathe, especially during an asthma attack.

The control means used in the apparatus 2 is able to control the operation of the apparatus such that it operates for predeterminable periods. These predeterminable periods may be timed periods in which case the control means will usually include timer means for causing operation of the apparatus 2 at predetermined times for predetermined periods. The timer means may be adjustable timer means or it may be a pre-set timer means. If desired, the control means may comprise an electronic sensor which causes the control means to operate consequent upon sensing a human. The electronic sensor is preferably an infrared electronic sensor. Other types of electronic sensors may however be employed.

The apparatus 50 may be a vacuum cleaner of a different shape to that shown. The control means 56 in the form of the push button switch may alternatively be a lever switch. Any suitable and appropriate type of chemical can be dispensed from the aerosol container 50, including liquids and powders. The chemical being dispensed may be dispensed from the dispensing head 66 in front of the rotating brush 68, or at any other desired position. A pipe (not shown) may be employed for enabling chemical to be dispensed into a dust bag 70 of the apparatus 50. The connection from the control means 56 to the solenoid 54 is shown as a cable 72 but other connecting means may be employed.

What is claimed is:

1. Apparatus for dispensing a chemical, which apparatus comprises an aerosol container which contains the chemical, electromagnetic means, and control means, the electromagnetic means being operable between a first state in which the chemical is not dispensed from the aerosol container and a second state in which the chemical is dispensed from the aerosol container, and the control means being such as to control the operation of the electromagnetic means such that the electromagnetic means is in the second state for predeterminable periods, and the apparatus being characterised in that the electromagnetic means extends around the aerosol container, and magnetically attractable material is provided for the aerosol container such that the aerosol container is able to be moved by the electromagnetic means for the purpose of dispensing the chemical from the aerosol container.

2. Apparatus according to claim 1 in which the aerosol container is made of a magnetically attractable material, or in which the aerosol container is made of a non-magnetically attractable material which is then provided with the magnetically attractable material, or in which the aerosol container is made of a non-magnetically attractable material and is held in a holder made of a magnetically attractable material.

3. Apparatus according to claim 1 and including a battery compartment for at least one battery for the electromagnetic means and the control means.

4. Apparatus according to claim 1 in which the control means is a manually operated switch.

5. Apparatus according to claim 1 and including a housing.

6. Apparatus according to claim 1 and including conduit means extending from the aerosol container to a position in which the chemical is required to be dispensed.

7. Apparatus according to claim 1 in which the electromagnetic means causes the aerosol container to move such that when the electromagnetic means goes from the first state to the second state then the aerosol container is caused to move to a position in which it releases the chemical, and when the electromagnetic means goes from the second state to the first state then the aerosol container is caused to move to a position in which it does not release the chemical.

8. Apparatus according to claim 7 in which the aerosol container has an outlet valve which is depressed when the aerosol container is caused to move to the position in which it releases the chemical.

9. Apparatus according to claim 7 in which the aerosol container is mounted on spring means which biases the aerosol container towards the position in which it releases the chemical.

10. Apparatus according to claim 9 in which the spring means is a coil spring.

* * * * *